United States Patent
Perrault et al.

(10) Patent No.: US 6,347,246 B1
(45) Date of Patent: Feb. 12, 2002

(54) ELECTROTRANSPORT ADHESIVE FOR IONTOPHORESIS DEVICE

(75) Inventors: James J. Perrault, Vista; George S. Heard, Escondido; Solomon E. Shenkute, San Diego, all of CA (US)

(73) Assignee: Axelgaard Manufacturing Company, Ltd., Fallbrook, CA (US)

(*) Notice: Subject to any disclaimer, the term of this patent is extended or adjusted under 35 U.S.C. 154(b) by 0 days.

(21) Appl. No.: 09/497,097

(22) Filed: Feb. 3, 2000

(51) Int. Cl.$^7$ .......................... A61N 1/30; C25B 11/04; H01B 1/00
(52) U.S. Cl. ........................ 604/20; 204/291; 252/500
(58) Field of Search ................. 604/20, 501; 204/291; 252/500; 128/798, 802, 803; 424/484, 486; 514/944

(56) References Cited

U.S. PATENT DOCUMENTS

| | | | |
|---|---|---|---|
| 4,973,303 A | 11/1990 | Johnson et al. | 604/20 |
| 5,234,992 A | 8/1993 | Gyory et al. | 525/57 |
| 5,240,995 A | 8/1993 | Gyory et al. | 525/57 |
| 5,344,394 A | 9/1994 | Gyory et al. | 604/20 |
| 5,525,356 A | 6/1996 | Jevne et al. | 424/484 |
| 5,624,415 A | 4/1997 | Cormier et al. | 604/290 |
| 5,668,170 A | 9/1997 | Gyory | 514/449 |
| 5,766,144 A | 6/1998 | Lai et al. | 604/20 |
| 5,788,666 A | 8/1998 | Atanasoska | 604/20 |
| 5,800,685 A | 9/1998 | Perrault | 204/291 |
| 5,840,056 A | 11/1998 | Atanasoska | 604/20 |
| 5,857,993 A | 1/1999 | Atanasoska et al. | 604/20 |
| 5,871,461 A | 2/1999 | Atanasoska et al. | 604/20 |
| 5,941,843 A | 8/1999 | Atanasoska et al. | 604/20 |

OTHER PUBLICATIONS

"Experimental Studies In The Causes And Prevention of Iontophoretic Burns" Molitor & Fernandez Am J. Med Sci vol. 198 pp 778–785 (1939).

*Primary Examiner*—Sharon Kennedy
(74) *Attorney, Agent, or Firm*—Walter A. Hackler

(57) ABSTRACT

The present invention provides an electrically conductive adhesive hydrogel comprising from about 15 to about 60%, by weight of a cationic polymer prepared by the polymerization of a monomer having the formula:

$$\text{H}_2\text{C}=\overset{\text{H}}{\underset{\text{C}}{\mid}}-\overset{\text{O}}{\underset{\|}{\text{C}}}-\text{O}-(\text{CH}_2)_m-\overset{R_1}{\underset{R_2}{\overset{\mid}{\text{N}^+}}}-R_3 \quad X^-$$

wherein m is an integer of from 1 to 3; $R_1$, $R_2$ and $R_3$ are selected from the group consisting of H and hydrocarbyl radicals having from 1 to 15 carbon atoms and $X^-$ is an anion and from about 5 to less than about 40% water, by weight. This electrically conductive adhesive hydrogel is useful in the manufacture of medical devices, e.g. medical electrodes, and in particular, in iontophoretic medicament delivery devices wherein said polymer may function as a scavenger of hydroxyl ions generated during iontophoresis.

19 Claims, 1 Drawing Sheet

ELECTROTRANSPORT ADHESIVE FOR IONTOPHORESIS DEVICE

BACKGROUND OF THE INVENTION

1. Field of the Invention

The present invention relates to an ion-conducting adhesive composition that is suitable for skin contact during electrotransport of direct current stimulation and/or drug delivery. This adhesive composition minimizes the generation of electrolysis products such as hydrogen ions and/or hydroxyl ions, during use, thereby reducing pain and irritation of the skin. In the grounding position of a constant current drug delivery circuit, the adhesive composition will create a relative increase in the voltage gradient behind the drug. The adhesive composition is sufficiently weight bearing to hold small appliances and reserves for stimulation and/or drug delivery to the skin yet removes easily without leaving residue or causing irritation to the skin.

2. Description of the Art

Presently electrically conductive adhesive solid hydrogels and liquid gels are used in the medical field to provide an electrical interface to the skin of a subject to couple electrical signals into and/or out of the subject (e.g. for diagnostic and/or monitoring uses) and/or to couple electrical stimulus into the subject (e.g. for treatment and/or preventative uses.)

Perrault in U.S. Pat. No. 5,800,685 discloses hydrogels which include 40% or more, by weight, water and are particularly suitable for use in electronic medical devices such as sensing electrodes which are used for recording or monitoring, e.g. for ECG (electrocardiogram), EEG (electroencephalogram), and/or EMG (electromyogram), or as stimulation electrodes which are used to stimulate a subject, e.g. for transcutaneceous electrical nerve stimulation, for wound healing, for muscle stimulation (e.g. for physical therapy), for external pacing, for defibrillation or as electrosurgical and/or ablation grounding electrodes, or as electrotransport electrodes, e.g. for the iontophoresis or electrophoresis of drugs into a subject.

In particular, the technique of iontophoresis employs an electric field to mobilize ionic medicaments through the skin. This therapeutic modality allows for the introduction of substances into the tissues and blood stream of a patient without the necessity of hypodermic injection and its concomitant untoward effects, such as pain and risk of infection. Delivery of drugs via iontophoresis also presents the advantage of avoiding first-pass metabolism of a medicament. When a medicament is taken orally and absorbed from the digestive tract into the blood stream, the blood containing the medicament first percolates through the liver, a metabolically active organ, before entering the general circulation for delivery to the target tissue. Thus, much of the orally ingested medicament may be metabolically inactivated before it has a chance to exert its pharmacologic effect.

The usefulness of electrodes in medical procedures is limited, however, by a finite incidence of skin burns resulting from the passage of current through the skin. The primary causative factor of this skin burning is an electrochemical mechanism whereby the applied current causes electrolysis of water and generates either H+or OH$^-$ ions, which cause pH changes that ultimately lead to a burning of the skin under the electrode. For example, in an iontophoresis procedure to mobilize a positively charged medicament through the skin, the medicament will be placed at the anode or positive electrode A negatively charged electrode or cathode will act as an indifferent or counter electrode. When current is applied to the iontophoresis system, the medicament will be driven toward and through the skin, but the application of the current at the positive electrode will also cause the following reaction:

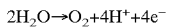

The H$^+$ ions will move rapidly to the skin, decrease the pH of the aqueous environment to dangerous levels, and ultimately cause a burning of the skin. At the cathode, in this example, the indifferent or counter electrode, the following reaction occurs:

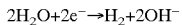

The OH$^-$ ions move rapidly to the skin, increase the pH of the aqueous environment at the electrode to dangerous levels, and ultimately cause a burning of the skin under the negative electrode. In an iontophoresis procedure to mobilize a negatively charged medicament through the skin, the same reactions will occur at the anode and cathode, with the cathode impregnated with the medicament ions and the anode acting as the indifferent or counter electrode. In a typical application of current through electrodes in contact with the skin, the pH under the anode decreases to less than 1.5 (acidic), and the pH under the cathode increases to exceed 10 (basic). Application of current in an iontophoresis procedure, then, not only mobilizes the ionic medicament across the skin, but also causes the electrolysis of water and the generation of reactive H$^+$ and OH$^-$ ions that cause a burning of the skin. In addition, a substantial amount of current is wasted in driving the H$^+$ and OH$^-$ ions and the presence of these ionic species in the iontophoretic system aggravates the problem of quantification of the amount of medicament delivered during iontophoresis.

A substantial effort has been directed toward alleviating the problem associated with electrochemical burns in iontophoresis. One approach has been to introduce a buffer into the iontophoretic system. A buffer renders a solution more resistant to a change in pH following addition of acid (H$^+$) or base (OH$^-$) than does an equal volume of water. In this approach, a soluble buffer salt is included in the solution containing medicament ions.

This use of a buffer in an iontophoresis system, however, presents several problems. Firstly, buffer ion molecules and their complementary ions tend to be smaller and thus more mobile than the medicament ions. When current is applied to an iontophoretic system containing a buffer, the buffer ions will move more rapidly toward and through the skin than the medicament ions, and it is more difficult to quantify the amount of medicament driven through the skin. Although a buffer incorporated into an iontophoresis system could successfully scavenge undesirable H$^+$ and OH$^-$ ions and reduce burning of the skin, the problems associated with mobile buffer ions overcome any advantage this approach might have.

Various iontophoresis devices are known, some of which include approaches that attempt to solve the problems associated with the generation of irritating hydrogen and hydroxyl ions and/or the use of buffer systems based small molecules such as the common salts of weak acids and/or weak bases.

For example, U.S. Pat. No. 5,668,356 to Jevne et al discloses amphoteric copolymers having alternating acid and basic monomer units for use in iontophoresis devices.

Cormier et al in U.S. Pat. No. 5,624,415, discloses a method for minimizing skin irritation and/or erythema in an iontophoresis device by maintaining the anode reservoir at a pH about 4 and/or the cathode reservoir at a pH below 4 and/or monitoring the potassium efflux level in said reservoirs.

Gyory et al in U.S. Pat. Nos. 5,234,991; 5,240,995 and 5,344,394 disclose a two phase adhesive for use in an iontophoresis device comprising a hydrophilic polymer phase. In addition, Gyory et al in U.S. Pat. No. 5,668,170 disclose the use of "permeation enhancers" including quaternary ammonium salts to enhance electrotransport in an electrotransport delivery device.

Atanasoka et al disclose an iontophoresis device comprising a buffer component including a pH buffering agent heterogeneously dispersed in an absorbent material. The pH buffering agent may be an ion exchange material. See U.S. Pat. Nos. 5,857,993; 5,871,461 and 5,941,843. (See also, U.S. Pat. No. 4,973,303 to Johnson et al and U.S. Pat. No. 5,766,144 to Lai et al which also disclose the use of ion exchange resins as a pH buffer for an electrode useful in iontophoresis.) Atanansoka et al also disclose a pH buffered electrode which may be used in an iontophoresis device comprising a pH buffer chemically bonded to a foam. Said pH buffer may comprise a means for scavenging hydrogen ions without releasing ions, i.e. a "proton sponge". See U.S. Pat. Nos. 5,788,666 and 5,840,056; respectively.

Thus, it is clear that efforts continue to overcome the problems of skin irritation resulting from the use of iontophoresis devices, as well as other electrotransport devices which are utilized to transport medicaments through the skin of a subject.

SUMMARY OF THE INVENTION

The present invention provides an electrically conductive adhesive hydro gel comprising from about 15 to about 60%, by weight of a cationic polymer prepared by the polymerization of a monomer having the formula:

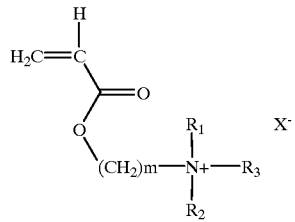

wherein m is an integer of from 1 to 3; $R_1$, $R_2$ and $R_3$ are selected from the group consisting of H and hydrocarbyl radicals having from 1 to 15 carbon atoms and $X^-$ is an anion and from about 5 to less than about 40% water, by weight.

The above polymer is of the formula

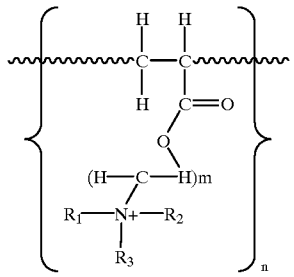

wherein m is an integer of from 1 to 3; $R_1$, $R_2$ and $R_3$ are selected from the group consisting of hydrogen and selected from the group consisting of H and hydrocarbyl radicals having from 1 to 15 carbon atoms, and n is a number greater than 1000.

In particular, the present invention provides an electrically powered iontophoretic medicament delivery device including a donor electrode assembly, a counter electrode assembly and a source of electrical power adapted to be electrically connected to the donor electrode assembly and the counter electrode assembly, the donor electrode assembly including the medicament reservoir containing the above hydrogel and the medicament reservoir being adapted to be placed in medicament transmitting relation with a body surface by adhering said medicament reservoir to said body surface by means of said hydrogel; and a donor electrode adapted to be electrically connected to the source of electrical power, the donor electrode being in electrical contact with the medicament reservoir.

DETAILED DESCRIPTION OF THE INVENTION

Figure 1:
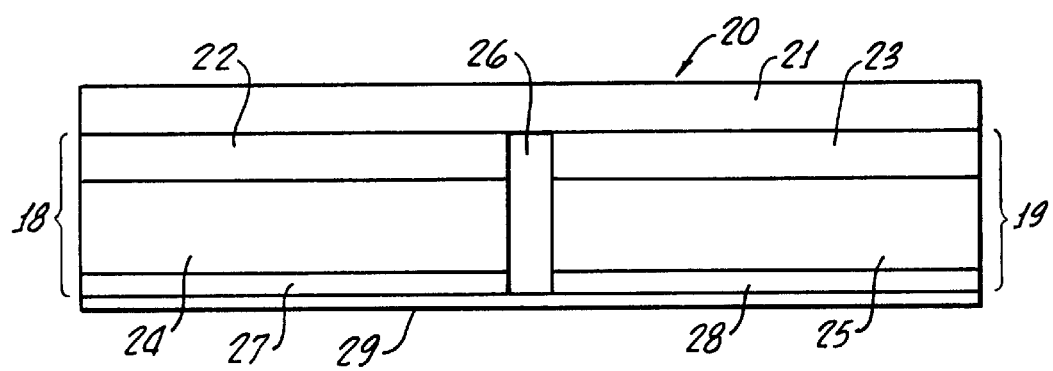
FIG. 1 is a schematic view of an iontophoretic delivery device of the present invention.

The preferred chemical formula for cationic acrylates suitable for the present invention is shown below wherein $R_1$, $R_2$ and $R_3$ are hydrogen or hydrocarbon groups and wherein $X^-$ is an anion.

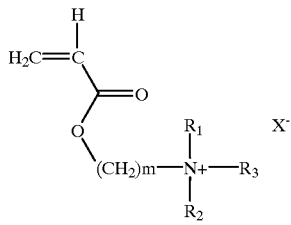

The preferred method for making an adhesive hydrogel including such cationic acrylates suitable for the present invention is described below.

Generally, the present hydrogel preferably includes between about 15 to 60% by weight polymer, more preferably between about 20 to 50% by weight polymer, and even more preferably between about 25 to 40% by weight of polymer and from 5 to no more than 40%, by weight water, preferably 5 to 10%, by weight water, e.g. 6 to 8%, by weight, water. The present hydrogel will have a pH from about 4 to about 9; preferably from about 6 to about 8.

When the hydrogel adhesives of the present invention are used in an iontophoresis device, due to the buffering quality of the polymer, itself, no buffer is usually necessary. However, small amounts of buffers used in the art may be added, if desired.

Specific examples of cationic acrylates which are commercially available are acryloyloxyethyltrimethyl ammonium chloride and acryloyloxyethyltrimethyl ammonium methyl sulfate which are available from Ciba Geigy Corporation.

The cationic acrylate hydrogels suitable for the present invention are preferably formed by in-situ free radical polymerization of a water soluble monomer (such as those shown above) in the presence of water, preferably by ultraviolet curing with initiator(s) and multi-functional crosslinking agent(s). For example, an appropriate cationic acrylate monomer (as shown above); water; optional additional conductor(s), e.g. salt, i.e., sodium chloride, potassium chloride, etc.; initiator or catalyst (e.g. 1-hydroxycyclohexylphenol ketone, etc.) and multifunctional cross-linker (e.g. methylene-bis-acrylamide, etc.) are combined, placed in a mold, and exposed to ultraviolet radiation as is known in the art. The result is a cationic acrylate hydrogel suitable for the present invention which is somewhat clear in color, viscous, and tacky to the touch. The hydrogel tends to be sufficiently adhesive to a subject's skin, yet sufficiently cohesive to be easily removable from the subject's skin and is inseparable from itself.

While not necessary, comonomers may be used with the above cationic monomers in the preparation of the hydrogel of the present invention including comonomers soluble in water, and, even more preferably including anionic comonomers so soluble. (The anionic comonomers may function as hydrogen ion or proton scavengers when the adhesive hydrogel is utilized in an iontophoresis device.) The amount of comonomer to be used is in the range of 5 to 30%, by weight, preferably 7 to 15%, by weight, based on the amount of reactants used. Examples of suitable co-monomers include: unsaturated organic carboxylic acids such as acrylic acid, methacrylic acid, maleic acid, itaconic acid, and citraconic acid and salts thereof, unsaturated organic sulfonic acids such as styrene sulfonic acid, methallyl sulfonic acid, 2-sulfoethyl acrylate, 2-sulfoethyl methacrylate, 3-sulfopropyl acrylate, 3-sulfopropyl methacrylate, acrylamide-2-methylpropane sulfonic acid and salts thereof, N, N-dimethylacrylamide, vinyl acetate, other radically polymerizable ionic monomers containing a carbon-carbon double bond, and non-N-vinyl lactam such as N-vinyl-2-pyrrolidone, N-vinyl-2-valerolactam, N-vinyl-2-caprolactam, and mixtures thereof. Among the ionic monomers enumerated above, particularly desirable selections are 3-sulfopropylacrylate or methacrylate, salts thereof, and 2-acrylamide-2-methyl propane sulfonic acid, and salts thereof. Examples of cations involved in the formation of such salts include sodium, potassium, lithium, and ammonium ions. The ionic monomers may be used singly or in a mixture of two or more monomers.

As is also mentioned above, other additives may be included in the present hydrogels, either before or after curing (i.e. conductivity enhancers, medicaments, humectants, plasticizers, thickening agents, etc.) The appropriateness of such additives is generally dependent upon the intended end use of the particular hydrogel. In general, the other additives (and amounts thereof) that may be incorporated in the present hydrogel and amounts thereof are disclosed in U.S. Pat. No. 5,868,136 to Fox, et al which is hereby incorporated by reference.

The addition of conductivity enhancers may be preferred even though the hydrogel of the present invention is a polyelectrolyte ionically disassociated in water and therefore, conductive. A lower specified quantity of polyelectrolyte (and a correspondingly lower viscosity) may be desired in situations such as, for example, when the hydrogel must wet around chest hair. In such cases, the addition of a conductivity enhancer may be useful.

Preferred conductivity enhancers are salts such as potassium chloride and sodium chloride. These salts are preferred since human bodies use these salts for conduction. Although chlorides tend to retard the polymerization of anionic polyelectrolytes, it has been discovered that increasing the concentrations of chlorides enhances the polymerization reactions of the present cationic polyelectrolytes. Additional examples of salts which may be appropriate are lithium chloride, lithium perchlorate, ammonium chloride, calcium chloride, and/or magnesium chloride. Other chloride salts, iodide salts, bromide salts, and/or halide salts may also be suitable.

Other salts, such as salts of weak organic acids, may be preferable. Those salts compatible with the human body and with the chemistry of the present hydrogel invention may be used a conductivity enhancers where the preferred chloride salts might interfere (i.e. corrode) aluminum and/or stainless steel metal components used to interface the hydrogel with medical equipment. Examples of salts which may be suitable, include sodium citrate or magnesium acetate.

While, as noted above, use of a conductivity enhancer is optional, the amount of conductivity enhancer in a hydrogel is preferably in the range of none to some amount which will enhance the conductivity of the hydrogel, which may be, for example, in the range of about 0 to 15%, by weight.

As is mentioned above, initiators are preferably used in the polymerization of the present hydrogels. Examples of initiators which may be used include, for example, IRGACURE® 184 (1-hydroxycyclohexyl phenyl ketone) and DAROCURE® 1173 ($\alpha$-hydroxy-$\alpha$-$\alpha$-dimethylacetophenone) which are both commercially available from Ciba-Geigy Corp. These UV catalysts are preferred because they are non-yellowing. Other initiators which maintain the preferred water-white and water-clear appearance of the present hydrogels are preferred. However, additional examples of initiators (which may be photo initiators or thermal initiators) may include benzoyl peroxide, azo-bis-isobutyro-nitrile, di-t-butyl peroxide, bromyl peroxide, cumyl peroxide, lauroyl peroxide, isopropyl percarbonate, methylethyl ketone peroxide, cyclohexane peroxide, t-butylhydroperoxide, di-t-amyl peroxide, dicumyl peroxide, t-butyl perbenzoate, benzoin alkylethers (such as benzoin, benzoin isopropyl ether, and benzoin isobutyl ether), benzophenones (such as benzophenone and methyl-o-benzoyl benzoate), acetophenones (such as diethyoxyacetophenone, p-t-butyltrichloro-acetophenone, p-dimethylaminoacetophenone), thioxanthones (such as xanthone, thioxanthone, 2-chlorothioxanthone, and 2-isopropyl thioxanthone), benzyl 2-ethyl anthraquinone, methylbenzoyl formate, 2-hydroxy-2-methyl-1-phenyl propane-1-one, 2-hydroxy-4'-isopropyl-2-methyl propiophenone, $\alpha$-hydroxy ketone, tetramethylthiuram monosulfide, allyl diazonium salt, and combinations of camphorquinone and ethyl 4-(N,N-dimethylamino) benzoate. Other initiators may be found in, for example, Berner, et al, "Photo Initiators-An Overview", J. Radiation Curing (April 1979), pp. 2–9.

The amount of initiator is preferably within the range of about 0.02 to 2.0% by weight based on total amount of monomer, and more preferably within the range of about 0.03 to 0.7% by weight based on total amount of monomer.

UV curing parameters to achieve desired polymer properties are well known to those skilled in the art. An initiator for the present purposes tends to operate by absorbing select wavelengths of UV light, and breaking down into free radicals to initiate polymerization. The wavelengths and curing area set the style of UV bulb used in the curing process. Inhibition of polymerization due to dissolved oxygen, monomer preservatives, or other components may be overcome by changing the power, by pulsing, and/or by using catalyst accelerators. The amount of residual monomer (after polymerization) is preferred to be less than about 3% for good biocompatibility.

As is also noted above, cross-linking agents are preferably used to cross-link the present hydrogels. Examples of multifunctional cross-linking agents which may be used include, for example, methylene-bis-acrylamide and diethylene glycol diacrylate which are both commercially available from, for example, Polysciences, Inc. Warrington, Pa Additional examples of cross-linking agents which may be acceptable for use in the present invention include ethylene glycol diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis(N-vinyl-2-pyrrolidone), trimethylolpropate trimethacrylate, glycerol trimethacrylate, polethylene glycol dimethacrylate, and other polyacrylate and polymethacrylate esters.

The amount of cross-linking agent is preferably within the range of about 0.02 to 2.0%, by weight, based on total amount of monomer, and more preferably within the range of about 0.2 to 0.7%, by weight, based on total amount of monomer.

The above hydrogel adhesives are especially useful in a iontophoresis application and/or device due to the low water content and the ability to remove hydrogen and/or hydroxyl ions to thereby avoid skin irritation. Thus, the present invention also provides an iontophoretic delivery device adapted to iontophoretically deliver an medicament preferably in the form of ions, through a body surface such as intact skin or a mucosal membrane.

When the adhesive hydrogels of the present invention are used in an iontophoretic device, a medicament may be incorporated in the hydrogel, itself, or in a separate medicament reservoir adjacent the hydrogel. Both ionic and nonionic drugs in all therapeutic areas can be carried in the hydrogel including, but not limited to, antiinfectives (e.g. gentamicin sulfate, neomycin sulfate, or cephalosporin), analgesics, anesthetics (e.g. lidocaine hydrochloride or benzocaine), antihistamatic agents, anticonvulsants, antidepressants, antidiabetic agents, antidiarrheals, antihistamines, antiinflammatory agents, (corticosteroids, such as hydrocortisone, dexamethasone, betamethasone, triamcinolone acetonide, or fluocinonide), antinauseants, antispasmodics, anticholinergics, sympathomimetrics, xanthine derivatives, cardiovascular preparations, including calcium channel blockers, beta blockers, antianytlircs, antihypertensives, diuretics, vasodilators, including general, coronary, peripheral and cerebral central nervous system stimulants, diagnostics and the like.

These medicaments will be incorporated in the adhesive hydrogels of the present invention in an amount sufficient to obtain the desired effect during the iontophoresis procedure.

The delivery device of the present invention includes a donor electrode assembly, a counter electrode assembly and a source of electrical power adapted to be electrically connected to the donor electrode assembly and the counter electrode assembly. The donor electrode assembly includes an medicament reservoir containing the medicament to be delivered. The medicament reservoir is adapted to be placed in medicament transmitting relation with a body surface. The donor electrode assembly also includes a donor electrode adapted to be electrically connected to the source of electrical power. The donor electrode is also in electrical contact with the medicament reservoir.

The medicament-conducting adhesive is disposed between the donor electrode assembly and the body surface in order to adhere the electrode assembly to the body surface.

Preferably, the iontophoretic agent delivery device includes a counter electrode assembly having an electrolyte reservoir and a counter electrode in electrical contact with one another. The electrolyte reservoir in the counter electrode assembly is adapted to be placed in electrolyte transmitting relation with the body surface spaced apart from the donor electrode assembly. The electrolyte-conducting adhesive is disposed between the electrolyte reservoir and the body surface.

As used herein "iontophoresis" is defined as the mechanism by which drugs are transported through a body surface under the influence of an electrical field.

The term "body surface" as used herein, is defined as including without limitation, skin, body tissues, mucosal membranes, nails and blood vessel walls. As used herein, the expression medicaments intended to have its broadest interpretation as any therapeutically active substance which is delivered to a living organism to produce a desired, usually beneficial effect.

FIG. 1 shows one example of an electrically powered iontophoretic agent delivery device which utilizes the adhesive of the present invention. Device 20 is adapted to iontophoretically deliver a medicament through a body surface such as intact skin or a mucosal membrane. The delivery device 20 includes a donor electrode assembly 18 and a counter electrode assembly 19. Electrode assemblies 18 and 19 are separated from one another by an electrical insulator 26. Device 20 has a top layer 21 which contains a source of electrical power (e.g. a battery) adapted to be electrically connected to the donor electrode assembly 18 and the counter electrode assembly 19. The donor electrode assembly 18 includes an medicament reservoir 24 containing the medicament to be delivered. The medicament reservoir 24 is adapted to be placed in medicament transmitting relation with a body surface. The donor electrode assembly 18 also includes a donor electrode 22 adapted to be electrically connected to the source of electrical power. The donor electrode 22 is also in electrical contact with the medicament reservoir 24.

The medicament-conducting adhesive 27 is disposed between the donor electrode assembly 18 and the body surface in order to adhere the electrode assembly 18 to the body surface.

Iontophoretic medicament delivery device 20 includes a counter electrode assembly 19 having an electrolyte reservoir 25 and a counter electrode 23 in electrical contact with one another. The electrolyte reservoir 25 in the counter electrode assembly 19 is adapted to be placed in electrolyte transmitting relation with the body surface spaced apart from the donor electrode assembly 18. The electrolyte-conducting adhesive 28 is disposed between the electrolyte reservoir 25 and the body surface.

The device 20 also includes a strippable release liner 29 which is removed just prior to applying the device to a patient's body surface, e.g., skin.

We will now turn to specific exemplary embodiments of cationic acrylate hydrogel adhesives of the present invention and their use in an iontophoresis device.

EXAMPLE 1

| solid (gm) | water (gm) | Chemical |
|---|---|---|
|  | 20.00 | Distilled Water |
| 3.00 |  | KCl |
| 30.00 |  | Glycerin$_1$ |
| 10.00 |  | PEG 300$_1$ |
| 1.50 | 1.5 | K-732 |
| 7.08 |  | Acrylic Acid |
| 16.00 | 4.0 | FA1Q80BC$^1$ |
| 1.00 |  | K$_2$HPO$_4$ |
| 2.00 |  | NVP$^2$ |

-continued

| solid (gm) | water (gm) | Chemical |
|---|---|---|
| 3.00 | | DMSO[1] |
| 0.70 | | Irgacure 2959[1] |
| 0.22 | | SR-252[1] |
| 74.5 | 25.5 | |
| Total | 100 | |

[1] See Below
[2] N-vinylpyrollidone copolymer (thickener)

The above mixture was gelled as discussed below in Example 3. For the adhesive gel prepared in this Example, the 1000 Hz Volume Resistivity was 310 ohm-cm and the stainless steel peel was 170 grams/in.

EXAMPLE 2

| solid (gm) | water (gm) | Chemical |
|---|---|---|
| | 16.00 | Distilled Water |
| 3.20 | | KCl |
| 40.00 | | Glycerin |
| 1.50 | 1.5 | K-732[1] |
| 7.08 | | Acrylic Acid |
| 19.00 | 4.8 | FA1Q80BC[1] |
| 2.20 | | NVP[2] |
| 3.00 | | DMSO[1] |
| 0.70 | | Irgacure 2959[1] |
| 0.22 | | SR-252[1] |
| 76.90 | 23.10 | |
| Total | 100 | |

[1] See Below
[2] See Above

The above mixture was gelled as discussed below in Example 3. The 1000 Hz Volume Resistivity was 370 ohm-cm and the stainless steel peel was 190 grams/in.

EXAMPLE 3

| solid (gr) | water (gr) | Chemical |
|---|---|---|
| 24.00 | 6.00 | Adamquat BZ 80[1] |
| 25.00 | | Neutrol TE[2] |
| 17.00 | | PEG 300[7] |
| 10.7 | | Acrylic Acid |
| 12.00 | | Glycerine |
| 1.5 | | DMSO[3] |
| 2.25 | 0.75 | 75% PGP[4] |
| 0.4 | | Irgacure 2959[5] |
| 0.4 | | SR 252[6] |
| 93.25 | 6.75 | |
| Total | 100 | |

[1] Acryloxyethyldimethylbenzyl Ammonium Chloride
[2] N,N,N',N'-Tetrakis (2-hydroxypropyl)ethylene diamine
[3] Dimethylsulfoxide
[4] Potassium glycerophosphate
[5] 2-Hydroxy-1-[4-(hydroxyethoxy)phenyl]-2-methyl-1-propanone
[6] Polyethylene Glycol 600 Dimethacrylate
[7] Polyethylene glycol, M.W. 300

These starting materials were mixed in the order given above and placed under a UV Lamp. Temperature was 25° C. and pH was 6.8.

The resulting gel had good adhesive and cohesive strength with little residue. The 1000 Hz Volume Resistivity was 20,000 ohm-cm which is ideal for iontophoresis and the stainless steel peel was 2.5 lbs./in. The resulting gel was tested and passed standards testing for biocompatibility and electrical properties as developed by the Association for the Advancement of Medical Instrumentation (AAMI) and accepted by the American National Standards Institute with the exception of 10 Hz impedance which was about 5,000 ohms for example 3 as well as 4 and 5, below.

The resulting gel has excellent resistance to hydrolysis when utilized in the device of FIG. 1, as a result of the low water content, i.e. 6.75%, and the use of Adamquat BZ80 as a hydroxyl radical scavenger alleviated skin irritation resulting from any hydrolysis that did occur. This acrylic ester is easy to cure with UV radiation which is the preferred method of preparing the hydrogel adhesives of this invention. Other quaternary acrylic ester monomers may be used in the adhesive hydrogels of this invention, however, this benzyl derivative is preferred because carbon loaded plastic films are often used in iontophoresis return electrodes and the benzyl derivative has good affinity (adhesion) to carbon loaded plastics. Also, the benzyl group may scavenge any carbon radicals before they reach the skin. Neutrol TE is used to scavenge protons or hydrogen ions resulting from hydrolysis. Other primary amines, in amounts ranging from about 1 to about 40%, by weight, preferably about 10 to about 30%, by weight, of the hydrogel, may also be used as a proton or hydrogen ion scavenger. Neutrol TE is preferred because of its large molecular size (limited motion) and biocompatibility. Neutrol TE also has humectant/plasticizer properties.

The adhesive hydrogel of this Example is utilized in the iontophoresis device of FIG. 1 with the following results:

As direct current is driven through the body, water in the adhesive hydrogel and skin undergoes electrolysis. When the cathode exceeds pH 10, burning begins. Caustic burns are far worse than the acid burns at the anode and in extreme cases the damage can be permanent scarring. It is found in external pacing studies on pigs using a biphasic DC wave form of 200 milliamps that the adhesive hydrogel of Examples 1 and 2 prevents caustic burns.

When the adhesive hydrogel of this Example is applied to the return or counter electrodes used in the iontophoresis of lidocaine the treatment is found to be less painful due to hydroxyl radical scavenging. Reducing the water content reduces the pain further. The amount of transient erythema (temporary redness) is also reduced. It is believed that this result is due to reduced electrolysis as evidenced by less gas bubbles generated at the electrical conductor/ionic conductor interfaces. (Hydrogen is generated at the cathode and oxygen at the anode by the electrolysis of water.) When the water content is lowered to an amount as low as feasibly possible, if the hydrogel is prepared by a simple mix and cure process, even less pain is experienced by the patient.

In general, about 5 to 6%, by weight, water is the lower limit for preparing the hydrogel in a simple mix and cure process.

The adhesive hydrogel of this Example when used in a return electrode for iontophoresis is better than the standard-of-care electrode utilizing an adhesive which is a Karaya gum with 12% water and a Ringer's lactate buffer system. The advantages are a consistent synthetic material less painful to use in iontophoretic treatments that has improved electrical contact through better skin adhesion and less gas generation at electromotive interfaces.

EXAMPLE 4

| solid (gr) | water (gr) | Chemical |
|---|---|---|
| 24 | 6 | FA1Q80BC[1] |
| 20 | | Neutrol TE |
| 22 | | PEG 300 |
| 8.6 | | Acrylic Acid |
| 10 | | Glycerine |
| 2 | | DMSO |
| 4.5 | 1.5 | 75% PGP |
| 0.7 | | SR-344[8] |
| 0.7 | | Irgacure 2959 |
| 92.5 | 7.5 | |
| Total | 100.0 | |

The pH of the solution was 6.70 and the pH of the resulting gel was 7.10.
[1]See above.
[8]Polyethylene Gycol 400 Dimethacrylate.

When this adhesive hydrogel is substituted for the adhesive hydrogel of Example 1 in an iontophoresis device, substantially equivalent results are obtained.

EXAMPLE 5

| solid (gr.) | water (gr.) | Chemical |
|---|---|---|
| 18 | | Neutrol TE |
| 6.6 | | Acrylic Acid |
| 20.8 | 5.2 | FA1Q80BC |
| 5.25 | 1.8 | 75% PGP |
| 13 | | Glycerine |
| 24 | | PEG 300 |
| 2 | | DMSO |
| 0.7 | | Irgacure 2959 |
| 0.7 | | SR-344 |
| 1.0 | 1.0 | K-732[9] |
| 92.05 | 7.95 | |
| Total | 100.00 | |

The pH of the gel was 6.90.
[8]Goodrite K732 Polyacrylic Acid 500

When this adhesive hydrogel is substituted for the adhesive hydrogel of Example 1 in an iontophoresis device, substantially equivalent results are obtained.

EXAMPLE 6

The adhesive gels of Examples 1 through 5 are utilized as the return or counter electrode of an iontophoresis device to deliver pilocarpine nitrate to induce localized sweating of a cystic fibrosis patient for the purpose of analyzing such sweat for chloride ion. (Cystic fibrous patients have high chloride ion in their sweat.) The adhesive gels of Examples 1 and 2 pass the AAMI and ANSI electrical standards and do not burn dining external pacing studies of pigs. The adhesive gels of Examples 1 and 2, when used as counter or return electrode gels, cause greater irritation and less sweating at the pilocarpine gel donor site than the adhesive gels of Examples 3, 4 and 5. The pilocarpine loaded donor gel pad is unchanged. Also, when testing the above adhesive gels on pigs at 200 milliamps in the external pacing studies, as compared to 4 milliamps in human patients, there is less relative ionic motion in the adhesives of Examples 1 and 2 thereby demonstrating that even though the polyquatemary group of the cationic acrylates of the present invention scavenges hydroxyl ions, the water concentration must be low for best results in preventing iontophoresis pain and bums.

While the above examples illustrate specific embodiments of the hydrogel adhesives of the present invention, it is understood that such examples are not intended to be limiting, as obvious modifications thereof will be apparent to those skilled in the art and are intended to be included within the claims. In particular, the references cited above under the Description of the Art show iontophoresis devices which may be used with the hydrogel adhesives of the present invention and, therefore, such references are hereby incorporated by reference for that purpose.

What is claimed is:

1. An electrically conductive adhesive hydrogel comprising from about 15 to about 60%, by weight of a cationic polymer prepared by the polymerization of a monomer having the formula:

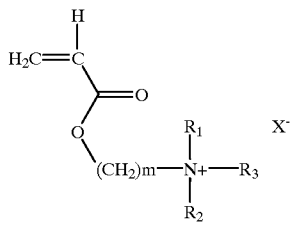

wherein m is an integer of from 1 to 3; $R_1$, $R_2$ and $R_3$ are selected from the group consisting of H and hydrocarbyl radicals having from 1 to 15 carbon atoms and $X^-$ is an anion and from about 5 to less than about 40% water, by weight.

2. The hydrogel of claim 1 wherein the polymer has the formula

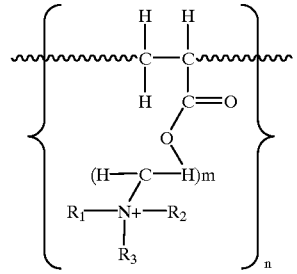

wherein m is an integer of from 1 to 3; $R_1$, $R_2$ and $R_3$ are selected from the group consisting of hydrogen and selected from the group consisting of H and hydrocarbyl radicals having from 1 to 15 carbon atoms, and n is a number greater than 1000.

3. The hydrogel of claim 2 wherein m is 2 and $R_1$ and $R_2$ and $R_3$ are selected from the group consisting of phenyl and $CH_3$.

4. The hydrogel of claim 2 wherein the monomer polymerized is acryloxyethyldimethylbenzyl ammonium chloride.

5. The hydrogel of claim 1 where $X^-$ is a chloride or sulfate anion.

6. The hydrogel of claim 1 comprising from about 20 to about 50% by weight of said cross-linked cationic acrylate polymer.

7. The hydrogel of claim 1 comprising about from 25 to about 40% by weight of cross-linked cationic acrylate polymer.

8. The hydrogel of claim 1 further comprising up to about 10% by weight water.

9. An electrode comprising an electrically conductive adhesive hydrogel comprising from about 15 to about 60%, by weight of a cationic polymer prepared by the polymerization of a monomer having the formula:

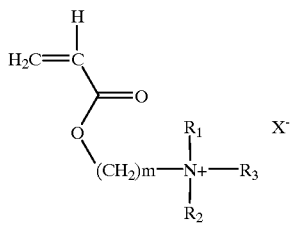

wherein m is an integer of from 1 to 3; $R_1$, $R_2$ and $R_3$ are selected from the group consisting of H and hydrocarbyl radicals having from 1 to 15 carbon atoms and $X^-$ is an anion and from about 5 to less than about 40% water.

10. A medical device comprising the electrode of claim 9.

11. A medical device comprising the adhesive hydrogel of claim 1.

12. The medical device of claim 10 further comprising a medicament.

13. The medical device of claim 11 further comprising a medicament.

14. The hydrogel of claim 1 further comprising a medicament.

15. An electrically powered iontophoretic medicament delivery device including a donor electrode assembly, a counter electrode assembly and a source of electrical power adapted to be electrically connect to the donor electrode assembly and the counter electrode assembly, the donor electrode assembly including:

(a) a medicament reservoir containing the hydrogel of claim 14, the medicament reservoir adapted to be placed in medicament transmitting relation with a body surface by adhering said medicament reservoir to said body surface by means of said hydrogel; and (b) a donor electrode adapted to be electrically connected to the source of electrical power, the donor electrode being in electrical contact with the medicament reservoir.

16. The hydrogel of claim 2 further comprising from about 1 to about 40%, by weight of a primary amine as a proton or hydrogen ion scavenger.

17. The hydrogel of claim 16 wherein said primary amine is N, N, N', N'-Tetrakis (2-hydroxypropyl) ethylene diamine.

18. The hydrogel of claim 17 comprising from about 6 to about 8% by weight, water.

19. An electrically conductive adhesive hydrogel comprising from about 15 to about 60%, by weight of a cationic polymer prepared by the polymerization of a monomer having the formula:

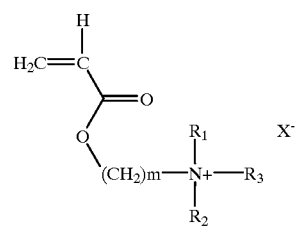

wherein m is an integer of from 1 to 3; $R_1$, $R_2$ and $R_3$ are selected from the group consisting of H and hydrocarbyl radicals having from 1 to 15 carbon atoms and $X^-$ is an anion and water in an amount ranging from no more than sufficient to polymerize said monomer in a simple mix and cure process up to no more than 40%, by weight.

* * * * *